US010442762B2

(12) United States Patent
Buzder-Lantos et al.

(10) Patent No.: US 10,442,762 B2
(45) Date of Patent: Oct. 15, 2019

(54) PROCESS FOR THE PREPARATION OF CARBOPROST AND ITS TROMETHAMINE SALT (71) Applicant: CHINOIN GYÓGYSZER ÉS VEGYÉSZETI TERMÉKEK GYÁRA ZRT., Budapest (HU)

(72) Inventors: Péter Buzder-Lantos, Budapest (HU); Zsuzsanna Kardos, Budapest (HU); Irén Hortobágyi, Budapest (HU); István Lászlófi, Budapest (HU); Imre Juhász, Budapest (HU); László Fónagy, Budapest (HU); Csaba Váradi, Budapest (HU); Ágnes Nagyné Borkó, Budapest (HU)

(73) Assignee: CHINOIN GYOGYSZER ES VEGYESZETI TERMEKEK GYARA ZRT., Budapest (HU)

(*) Notice: Subject to any disclaimer, the term of this patent is extended or adjusted under 35 U.S.C. 154(b) by 0 days.

(21) Appl. No.: 15/780,896

(22) PCT Filed: Nov. 10, 2016

(86) PCT No.: PCT/HU2016/000067
§ 371 (c)(1),
(2) Date: Jun. 1, 2018

(87) PCT Pub. No.: WO2017/093770
PCT Pub. Date: Jun. 8, 2017

(65) Prior Publication Data
US 2018/0362457 A1    Dec. 20, 2018

(30) Foreign Application Priority Data
Dec. 1, 2015    (HU) .................................. 1500584

(51) Int. Cl.
*C07C 405/00* (2006.01)
*B01D 15/26* (2006.01)
(Continued)

(52) U.S. Cl.
CPC .......... *C07C 405/00* (2013.01); *B01D 15/265* (2013.01); *B01D 15/426* (2013.01);
(Continued)

(58) Field of Classification Search
None
See application file for complete search history.

(56) References Cited

U.S. PATENT DOCUMENTS

| 3,728,382 A | 4/1973 | Bundy |
| 2010/0041912 A1* | 2/2010 | Bhide .................. C07C 51/367 560/61 |
| 2013/0190404 A1 | 7/2013 | Li et al. |

FOREIGN PATENT DOCUMENTS

| CN | 102816099 | * 12/2012 |
| IN | 185790 B | 4/2001 |

(Continued)

OTHER PUBLICATIONS

Yankee ("Total Synthesis of 15-Methylprostaglandins" J. Am. Chem. Soc., 96:18, 1974, p. 5865-5876) (Year: 1974).*

(Continued)

*Primary Examiner* — Amy C Bonaparte
(74) *Attorney, Agent, or Firm* — Birch, Stewart, Kolasch & Birch, LLP

(57) ABSTRACT

The subject of the invention is a novel process for the preparation of Carboprost tromethamine salt where alkylation the enone of the general formula (II) is carried out in the presence of a chiral auxiliary in aprotic solvent with a Grignard reagent. The methyl ester epimers of formula (VII)

(Continued)

are separated by gravity silica gel chromatography and the salt formation is carried out by using solid tromethamine base.

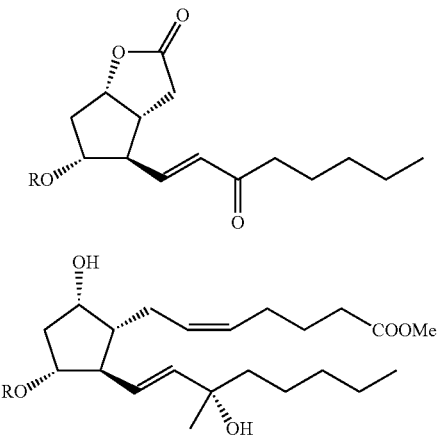

23 Claims, 6 Drawing Sheets

(51) Int. Cl.
 *B01D 15/42* (2006.01)
 *B01J 20/10* (2006.01)
 *C07C 7/12* (2006.01)
(52) U.S. Cl.
 CPC .............. *B01J 20/103* (2013.01); *C07C 7/12* (2013.01); *C07C 2601/08* (2017.05)

(56) References Cited

FOREIGN PATENT DOCUMENTS

WO   WO 2008/081191 A1   7/2008
WO   WO 2011/008756 A1   1/2011

OTHER PUBLICATIONS

Weber ("Enationnerically Pure Tertiary Alcohols by TADDOL-Assisted Additions to Ketones—or How to Make a Grignard Reagent Enantioselective" Angew. Chem. Int. Ed. Engl., 31, 1992, No. 1, p. 84-86) (Year: 1992).*
Hsi ("Synthesis of Tritium Labeled Arbaprostil and Related 15-Methyl Prostaglandins" Journal of Labelled Compounds and Radiopharmaceuticals, vol. XXV, No. 8, 1987, p. 865-878) (Year: 1987).*
De bruyn ("Mesoporous Zr and Hf catalysts for chemoselective MPV reductions of unsaturated ketones" Applied Catalysis A: General 254, 2003, p. 189-201) (Year: 2003).*
Trizma® Base, downloaded from https://www.sigmaaldrich.com/catalog/product/sigma/t4661?lang=en&region=US&cm_sp=Insite-_-prodRecCold_xviews-_-prodRecCold5-5# on Dec. 20, 2018 (Year: 2018).*
English translation of Hungarian Search Report, with a completion date of Jun. 14, 2016, for corresponding Hungarian Application No. P1500584.
English translation of the International Search Report (form PCT/ISA/210), dated Mar. 1, 2017, for corresponding International Application No. PCT/HU2016/000067.
International Preliminary Report on Patentability and English translation of the Written Opinion of the International Searching Authority (forms PCT/IB/373 and PCT/ISA/237), dated Jun. 5, 2018, for corresponding International Application No. PCT/HU2016/000067.
Lölsberg et al., "An Enantioselective Total Synthesis of Helioporins C and E," Organic Letters, vol. 14, No. 23, 2012 (Published on Web Nov. 13, 2012), pp. 5996-5999.

* cited by examiner

Fig. 1.

PRIOR ART

Fig. 2.

PRIOR ART

Fig. 3.

PRIOR ART

Fig. 4.

PRIOR ART

TES = triethylsilyl-

Fig. 5.

PRIOR ART

Prior art

Fig. 6.

Prior art

PROCESS FOR THE PREPARATION OF CARBOPROST AND ITS TROMETHAMINE SALT

The subject of the invention is a novel process for the preparation of Carboprost of formula I and Carboprost tromethamine of formula Ia.

Carboprost tromethamine is the original product of Upjohn. Indication: termination of pregnancy and termination of after delivery bleeding (postpartum haemorrhage).

The first economical and scalable synthesis of Carboprost tromethamine was described by chemists of Upjohn (J. Am. Chem. Soc., 96(18), 5865-5876, 1974).

Figure 1:
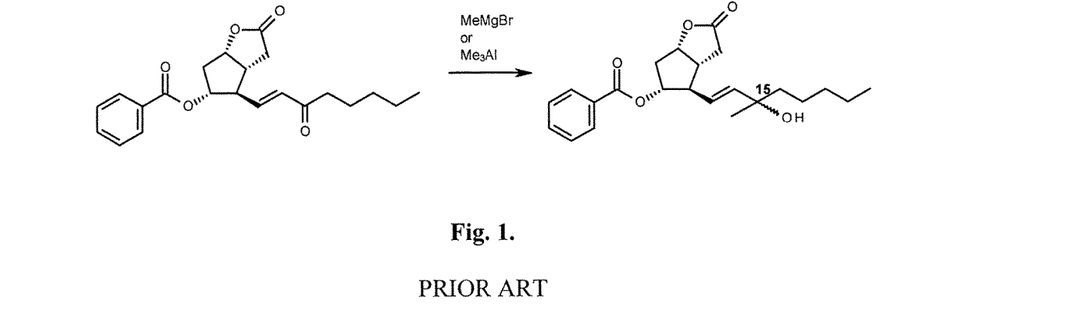
FIG. 1 is the prior art chemical reaction showing that the 15-methyl substituent was constructed from the benzoyl-enone with trimethylaluminum or with methylmagnesium bromide.

The 15-methyl substituent was constructed from the benzoyl-enone with trimethylaluminum or with methylmagnesium bromide (FIG. 1.).

The ratio of the 15-methyl-epimers was 1:1 in both cases. The epimers could not be separated by TLC method.

Figure 2:
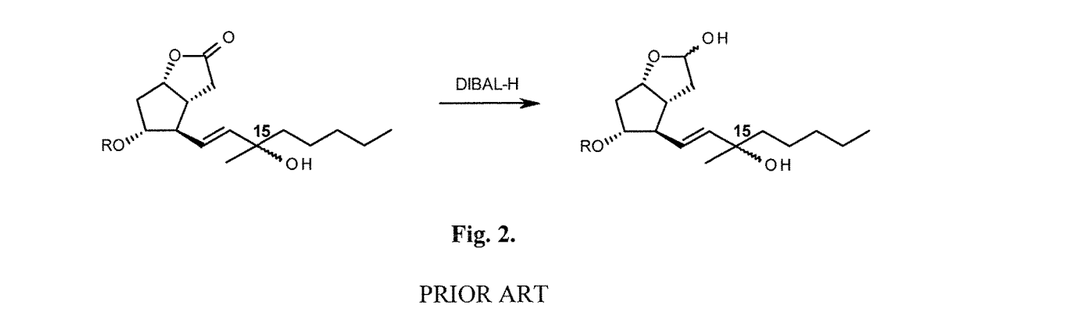
FIG. 2 is the prior art chemical reaction showing that the lactone group was reduced with diisobutylaluminum hydride.

In the next step the lacton group was reduced with diisobutylaluminum hydride. Lacton reduction was carried out from lacton epimers bearing R=benzoyl- or trimethylsilyl-protective group or R=H atom (FIG. 2).

Figure 3:
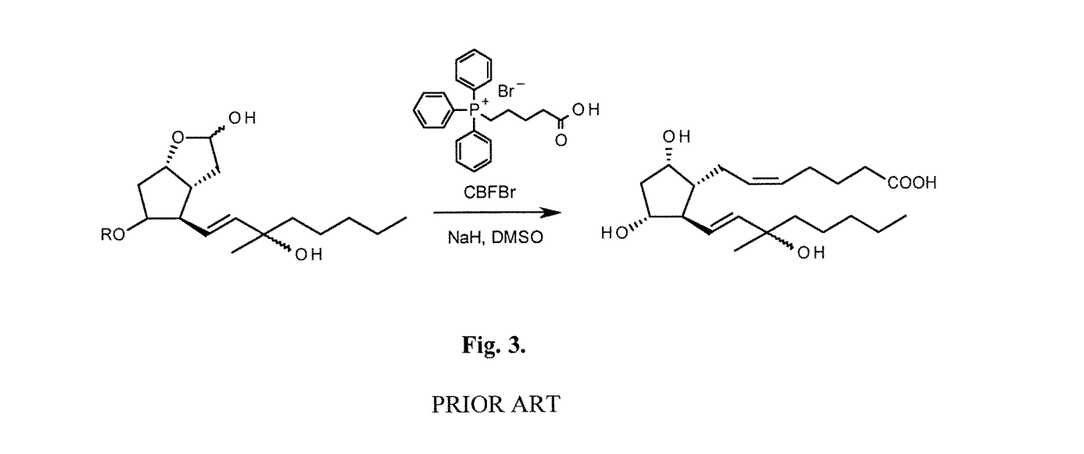
FIG. 3 is the prior art chemical reaction showing that an upper chain was formed by a Wittig reaction from all three lactol epimers.

The upper chain was formed by Wittig reaction from all three lactol epimers (FIG. 3.). The protecting group was removed during the work-up procedure and in each case the (R,S) Carboprost epimers were obtained. From the carboxybutylphosphonium bromide (CBFBr) the phosphoran was liberated with NaH/DMSO reagent.

Figure 4:
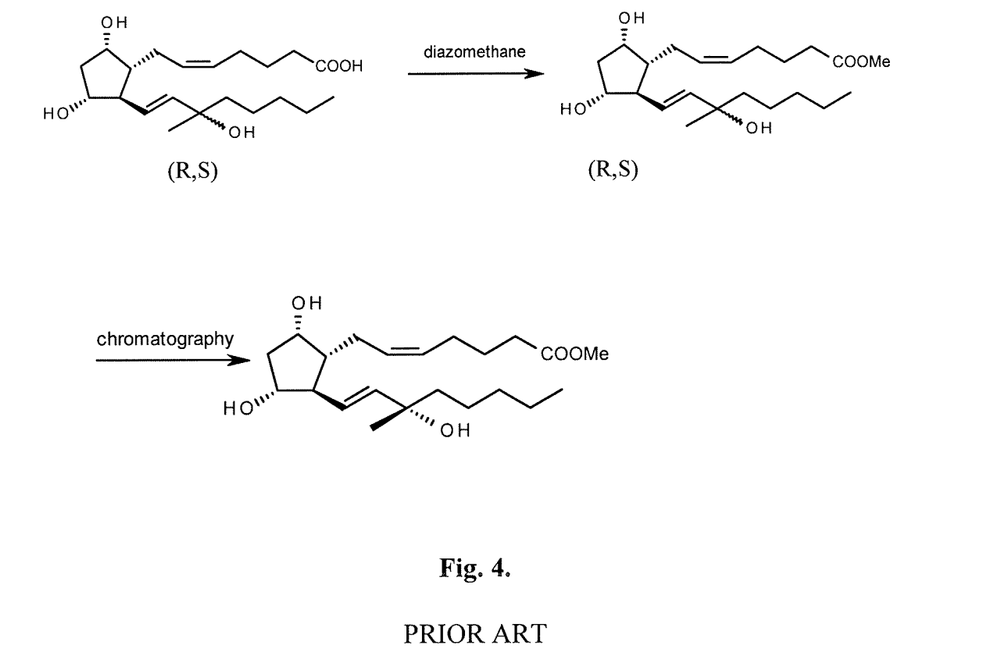
FIG. 4 is the prior art chemical reaction showing that the (R, S) Carboprost epimeric mixture was esterified with diazomethane and the (R,S) ester epimers were chromatographed using dichloromethane:acetone eluent mixture to obtain the Carboprost methyl ester.

The (R, S) Carboprost epimeric mixture was esterified with diazomethane and the (R,S) ester epimers were chromatographed using dichloromethane:acetone eluent mixture to obtain the Carboprost methyl ester (FIG. 4.).

According to patent specification IN 185790 A1 reduction of the oxo group of a PGE derivative with K- or L-selectride leads to PGF derivative which is a valuable intermediate in the synthesis of Carboprost methyl ester.

Patent specification IN 185790 A1 describes the preparation of Carboprost methyl ester starting from PGE derivative. Selective catalytic hydrogenation gives the respective PGE2 derivative which after reduction of the oxo group results the protected PGF2a derivative. In the last step the silyl protecting groups are removed to obtain the Carboprost methyl ester.

Figure 5:
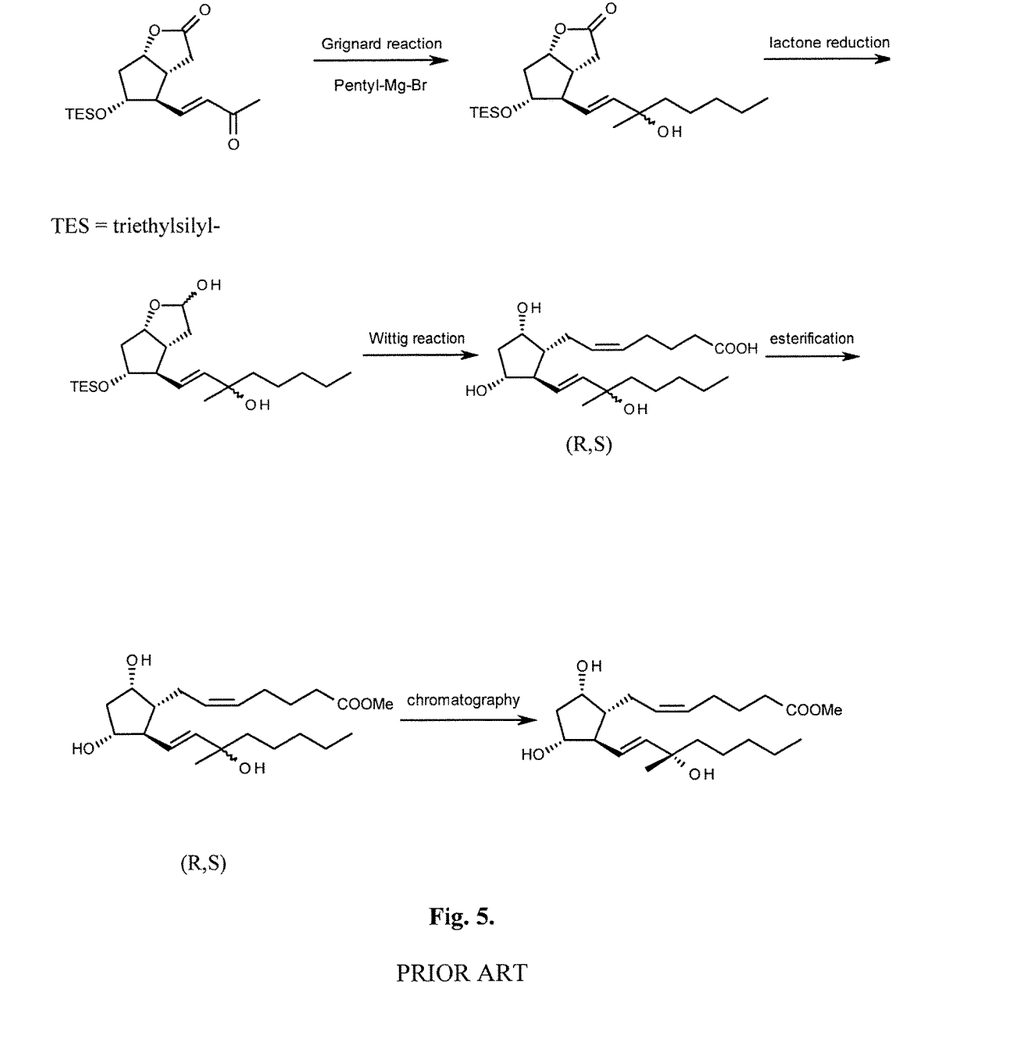
FIG. 5 is the prior art chemical reaction showing that, in patent specification WO2008/081191, Carboprost is prepared following the route described in J. Am. Chem. Soc., 96(18), 5865-5876, 1974.

In patent specification WO2008/081191 Carboprost is prepared following the route described in J. Am. Chem. Soc., 96(18), 5865-5876, 1974 (FIG. 5.).

Main advantages of the above process to prepare Carboprost methyl ester are as follows:

Grignard Reaction the enone was protected with triethylsilyl protecting group, instead of methylmagnesium bromide the more economical methylmagnesium chloride was used, the amount of the reagent was decreased from 16 molar equivalents to 5 molar equivalents, the applied solvent was toluene or xylene isomers, instead of THF.

As a result of these changes the ratio of the lacton epimers increased from 60:40 to 70:30, in favour of the desired epimer.

Lacton Reduction the amount of DIBAL-H was decreased from 4.6-5.4 molar equivalents to 3.5 molar equivalents.

Wittig Reaction

In the Wittig reaction the solvent (dimethyl sulfoxide) was not changed, but for the liberation of the phosphoran from the carboxybutyltriphenylphosphonium bromide (CBFBr), instead of NaH base, the less flammable and easier to handle NaNH2 was applied.

The temperature of the Wittig reaction was lowered from 20° C. to (−)-25-10° C. which resulted a decrease of the undesired trans epimer from 6-8% to 3%.

The triethylsilyl (TES) protecting groups cleaved during the work-up conditions of the Wittig reaction which is an additional benefit of using TES protecting group.

Esterification

Instead of the less scalable diazomethane method, the Carboprost epimers were esterified with dimethyl sulphate or methyl iodide in acetone, in the presence of potassium carbonate.

Due to these changes the yield of the Carboprost methyl ester epimers, starting from the protected enone increased from 55% to 75%.

Chromatography

For the separation of the Carboprost methyl ester epimers normal and reverse phase preparative HPLC methods were applied:

Normal phase preparative HPLC: Packing: Chiralpak AD

Eluent: mixtures of heptane or hexane and alcohols. Best separation was achieved with heptane:ethanol or heptane:isopropanol mixtures.

Reverse phase preparative HPLC:

Packing: Inertsil Prep ODS, Eluent: methanol:water:acetonitrile or

Packing: YMC C8, Eluent: methanol:water:acetonitrile

Two alternative synthetic routes were proposed.

In the first route the lacton epimers were separated by preparative HPLC method and the Carboprost methyl esters were prepared starting from the pure R and S epimers. Epimerisation during the process was not observed, but it was stated that preparative separation of the epimers is more favourable on the methyl ester level.

Figure 6:
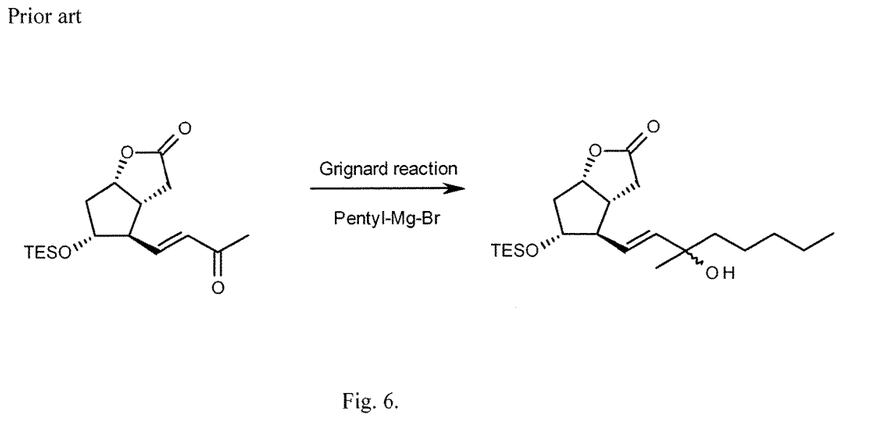
FIG. 6 is the prior art chemical reaction showing that, in the second route, the lower chain was constructed starting from the shorter-chain ketone using pentylmagnesium bromide.

In the second route the lower chain was constructed starting from the shorter-chain ketone using pentylmagnesium bromide (FIG. 6.).

The ratio of the lacton epimers on this route was 50:50%, this route therefore was ruled out.

Patent specification WO 2011/008756 A1 describes a general method for the synthesis of prostaglandins by metathesis connected with ring closure (Ring-Closing Metathesis, RCM reaction).

Figure 7:
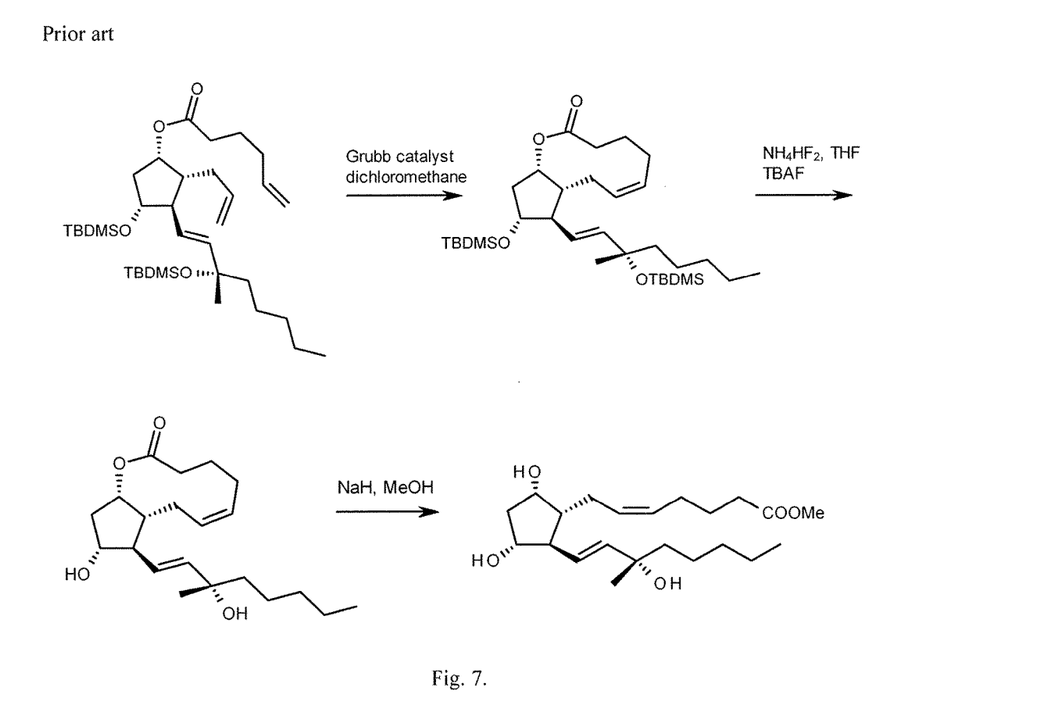
FIG. 7 is the prior art chemical reaction showing that, in the case of Carboprost, starting from the appropriate intermediate and using Grubb catalyst, the 1-9 lactone is prepared, which after removal of the protecting groups and opening of the lactone ring, gives the Carboprost methyl ester.

In the case of Carboprost, starting from the appropriate intermediate and using Grubb catalyst, the 1-9 lacton is prepared which after removal of the protecting groups and opening of the lacton ring gives the Carboprost methyl ester (FIG. 7.).

Advantage of the method is that the key intermediate is prepared from optically pure materials, therefore the resulting Carboprost methyl ester does not contain the R-epimer.

Disadvantages are that it applies reactions difficult to scale-up and uses chemically sensitive reagents.

Patent specification US2013/190404 publishes the X-ray diffraction and DSC data of Carboprost tromethamine. It describes the crystallisation: Carboprost is dissolved in solvent (acetonitrile, acetone, ether or C1-4 alcohol). To the solution the aqueous solution of tromethamine is added dropwise. The crystals are collected. Carboprost tromethamine is dissolved in water and after adding acetone the crystals are collected again.

Patent specification CN 102816099 A discloses the preparation of high purity Carboprost tromethamine.

Purification of the crude Carboprost ester was performed on the extremely expensive stationary phases, preferably 5-10 μm particle size, normal phase, cyano bonded or amino bonded or spherical silica gel. Application of these silica gels requires high pressure preparative liquid chromatography. This high pressure technology is time- and cost consuming, needs costly pressure proof equipments, high purity eluents and the listed expensive stationary phases.

Purity by HPLC ≥99.5%, 15-epi-epimer ≤0.5%, 5,6-trans isomer ≤0.5%.

The high purity ester is hydrolysed and from the acid the tromethamine salt is prepared.

We aimed to elaborate a method for the preparation of Carboprost tromethamine salt where the amount of the hardly removable 15-(R)-isomer (15-epi-Carboprost, ((R)-III)) impurity is not more than 0.5%.

The subject of our invention is accordingly a process for the preparation of Carboprost of formula I and its tromethamine salt of formula Ia in a way that the enone of the general formula II, wherein R stands for hydrogen atom or protective group, is selectively alkylated, the resulting enol of the general formula III wherein R has the meaning as defined above, is reduced, the R protecting group of the resulting lactol of the general formula IV is removed, from the thus obtained lactol epimers of formula V the Carboprost epimers of formula VI are prepared in Wittig reaction, the Carboprost epimers are transformed into the methyl ester, the methyl ester epimers of formula VII are separated by chromatography, the epimer of formula VIII is hydrolysed, and if desired, transformed into the tromethamine salt, characterized in that, a.) the selective alkylation is carried out in the presence of chiral additive, in aprotic organic solvent, with Grignard reagent, b.) chromatography is performed by gravity chromatography on silica gel, c.) tromethamine salt formation is carried out with solid tromethamine base.

In the process according to the invention as Grignard reagent methylmagnesium chloride or methylmagnesium bromide, preferably methylmagnesium bromide is applied, in an amount of 3-4 molar equivalents, preferably 3.5 molar equivalents.

As chiral additive complex-forming chiral additive, preferably (S)-Taddol may be applied, preferably in 1 molar equivalent amount.

As R protective group ether-, silyl ether-, benzyl-, substituted benzyl- or acyl-groups, preferably p-phenylbenzoyl group may be applied.

In the process according to the invention as aprotic organic solvent ethers, as diethyl ether, methyl tert-butyl ether, diisopropyl ether, tetrahydrofuran, methyltetrahydrofuran, dimethoxyethane; aromatic hydrocarbons, as benzene, toluene, xylene; halogenated solvents as dichloromethane, or mixtures of these solvents, preferably toluene is applied.

Methylation is carried out at a temperature between (−)-80-(−)-20° C., preferably at (−)-50° C.

According to the invention gravity silica gel chromatography may be performed in a manner that the applied eluent contains base, or a slightly basic/pH=7.5-8.0/silica gel is used.

As base an organic base or ammonia, preferably triethylamine may be used, where the amount of the base is preferably 0.1%. As eluent, dichloromethane:triethylamine or dichloromethane:acetone:triethylamine mixtures may be used.

As slightly basic silica gel for example 40-70 micrometer particle size Chromatorex MB spherical silica gel may be applied. As eluent, preferably acetone-dichloromethane gradient mixtures are used.

In the process according to the invention salt formation is carried out in water-free polar organic solvent, as for polar organic solvent alcohols and/or ketones, preferably isopropyl alcohol and/or acetone may be used.

Figure 8:
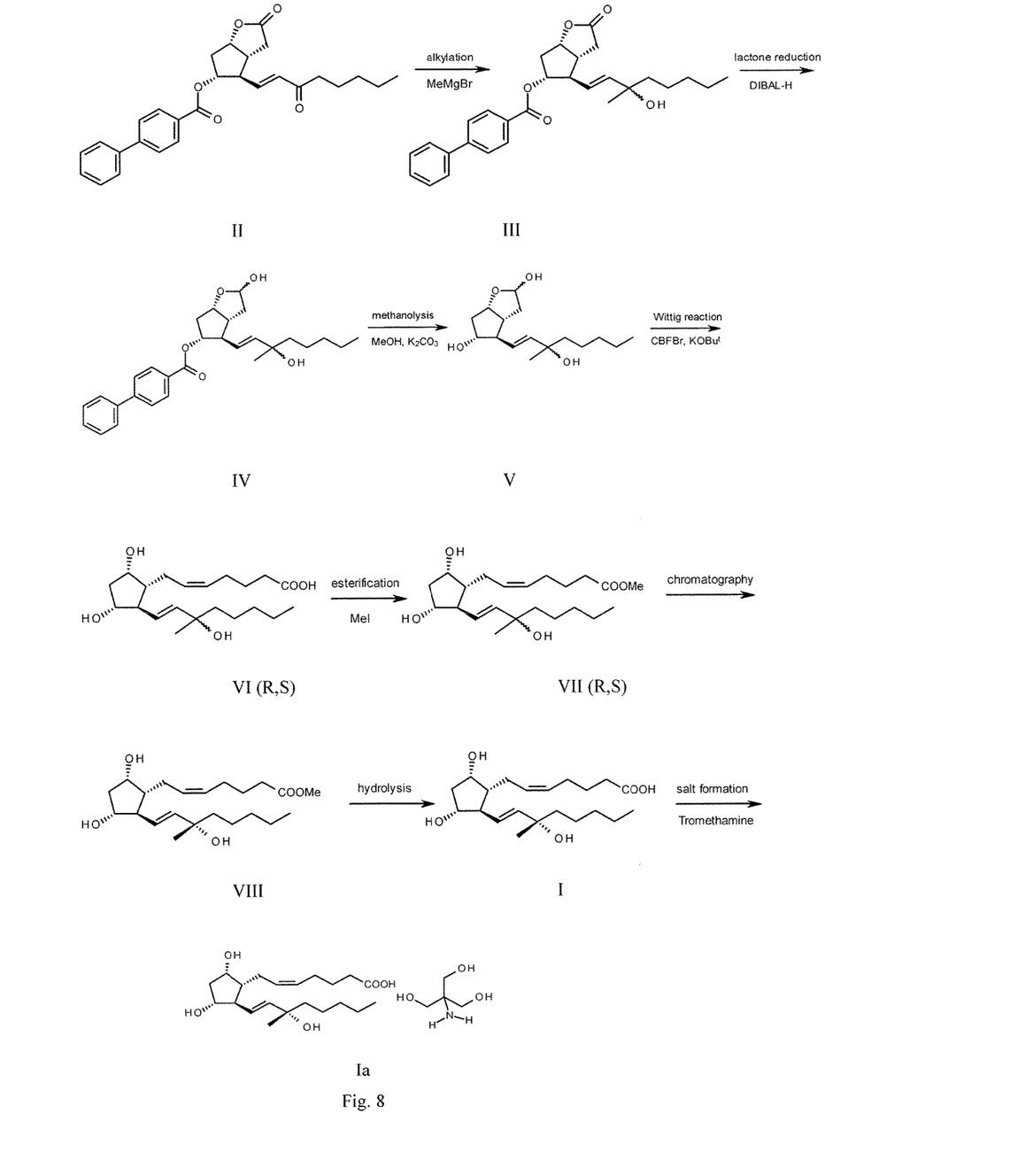
FIG. 8 is the chemical reaction showing the process according to the invention.

The process according to the invention is demonstrated in FIG. 8.

Significant advantage of the process according to the invention is that it produces Carboprost tromethamine salt where the amount of the hardly removable 15-(R)-isomer (15-epi-Carboprost impurity, derives from (R)-III epimeric impurity) is not more than 0.5%.

Impurity 15-(R) is formed in the first step of the synthesis during the alkylation by Grignard reaction.

The starting material of our process is the enone of formula II containing p-phenylbenzoyl protective group.

The key-step of the process is the alkylation of the enone of formula II. The higher stereoselectivity can be reached in the alkylation reaction, the smaller amount of the not-desired epimer ((R)-III) is formed and purification of the desired epimer ((S)-III) and further intermediates derived from it will also become easier and more economical.

In our process we aimed to realize the alkylation (methylation) as selectively as possible and remove the not-desired epimer as economically as possible.

Since the starting compound, the protected PG-enone is a chiral compound itself, in principle it is possible that the alkylation proceeds with good selectivity, without the addition of chiral additive, even though the reaction centre is relative far from the asymmetry centres. Good example for that is given in patent specification WO 2008/081191 A1, where a triethylsilyl-protected PG-enone was reacted in xylene, toluene or in the mixture of these solvents at −78° C. with 5 equivalents of methylmagnesium chloride. In the alkylation the very favourable epimer ratio of (S:R)=70:30 was achieved.

Selectivity of the reaction presumably depends on the reaction conditions (solvent, reaction temperature, reagent, sequence of addition) and on the structure of the starting material.

The PG-enone intermediate manufactured in the course of CHINOIN prostaglandin production contains p-phenylbenzoyl protecting group (II). Reaction of the enone with methylmagnesium bromide resulted, however, the (S)-III: (R)-III epimers in a ratio of 55:45.

Carrying out the alkylation with methylmagnesium bromide in toluene, in the presence of triethylamine, the low extent selectivity (55:45) did not change, and surprisingly, in the presence of the chiral S-dimethyl-1-phenylethylamine base, selectivity disappeared.

By additioning onto the PG-enone a reagent prepared from trimethylaluminum and 2,6-di-tert-butyl-4-methylphenol, the selectivity increased to 63:37.

In order to increase selectivity, the alkylation was performed in the presence of various chiral additives.

Possible chiral additives (Table 1.):

TABLE 1

|  |  |
|---|---|
| "(S)-Taddol" | (R)-Taddol |
| CAS No: 93379-49-8 | CAS No: 93379-49-7 |
| (4S,5S)-2,2-Dimethyl-α,α,α',α'-tetraphenyldioxolane-4,5-dimethanol | (4R,5R)-2,2-Dimethyl-α,α,α',α'-tetraphenyldioxolane-4,5-dimethanol |

Angew. Chem. Int. Ed., 40, 92-138 (2001)

D. Seebach, A.K. Beck, A. Heckel

TADDOLs, their derivatives and Taddole analogues, Versatile chiral auxiliaries

|  |  |
|---|---|
| CAS No: 18531-99-2 | CAS No: 18531-94-7 |
| (S)-(−)-1,1'-Bi(2-naphthol) | (R)-(−)-1,1'-Bi(2-naphthol) |

TABLE 1-continued

JACS, 124, 10336-10348
J. Balsells, T.J. Davis, P. Caroll, P.J. Walsh
Insight into the mechanism of the asymmetric addition of alkyl groups to aldehydes
catalyzed by titanium-BINOLate species CAS No: 115651-77-9
(1R,2S)-(+)-2-(Dibutylamino)-1-phenyl-1-propanol CAS No: 114389-70-7
(1S,2R)-(−)-2-(Dibutylamino)-1-phenyl-1-propanol J. Chem. Soc, Perkin I, 1991 (6) 1613-1615
K. Soai, Y. Kawase, A. Oshio
Enantioselective phenylation of prochiral aldehydes using a kinatically formed chiral
complex between Grignard-zinc halide reagent and N,N-dibutyl norephedrine CAS No: 869495-24-9
(S)-(+)-2-Piperidino-1,1,2-triphenylethanol CAS No: 213995-12-1
(R)-(−)-2-Piperidino-1,1,2,-triphenylethanol Tetrahedron Asymm, 15, 2085-2090 (2004)
N. Garcia-Delgado, M. Fontes, M.A. Percias, A. Riera, X. Verdaguer
Enantioselective addition of dimethylzinc to aldehydes: assessment of optimal N,N-
substitution for 2-dialkylamino-1,1,2-triphenylethanol ligands MIB
CAS No: 287105-48-0
(2S)-(−)-3-exo-(Morpholino)isoborneol
Chem. Comm, 1999, 1369-1370
W.A. Nugent
MIB: an advantageous alternative to DAIB
for the addition of organozinc reagents to
aldehydes "Szulfonamid"
CAS No: 470665-33-9
N,N'-(1S,2S)-(+)-1,2-cyclohexanediylbis[2-
hydroxy-7,7-dimethyl-
bicyclo[2.2.1]heptane-1-
methanesulfonamide]
Tetrahedron Asymm, 13, 2291-2293 (2002)
M. Yus, D.J. Ramon, O. Prieto
Highly enantioselective addition of
dialkylzinc reagents to ketones promoted by
titanium tetraisopropoxide In the case of methylmagnesium bromide alkylating agent the (S)-Taddol turned out to be the most efficient additive resulting a ratio of (S)-III:(R)-III=70:30, therefore we studied this reaction in details. The alkylation was carried out in ether-type and in halogenated solvents and in toluene.

The reactions were carried out at −50° C., because at lower temperatures, at (−)-70 and at (−)-80° C. the reaction slowed down, while the epimer ratio did not improve. At higher temperature, at (−)-25° C., many side-products appeared.

Effect of the (S)-Taddol amount on the (S)-III:(R)-III epimer ratio (Table 2.)

(Solvent: toluene, reaction temperature: (−)-50° C.)

TABLE 2

| (S)-Taddol molar equivalent | MeMgBr equivalency | Epimer ratio (S)-III:(R)-III | Estimated yield (%) |
|---|---|---|---|
| 0.25 | 4 | 57:43 | 99 |
| 0.5 | 4 | 58:42 | 95 |

TABLE 2-continued

| (S)-Taddol molar equivalent | MeMgBr equivalency | Epimer ratio (S)-III:(R)-III | Estimated yield (%) |
|---|---|---|---|
| 0.75 | 4 | 63:37 | 85 |
| 1.0 | 4 | 66:34 | 99 |
| 1.5 | 4.5 | 63:37 | 99 |

From the above results it reveals that the optimal amount of (S)-Taddol chiral auxiliary is 1 molar equivalent. Taking smaller amount the epimer ratio is less good, while a higher excess has no further effect.

Effect of solvents on the (S)-III: (R)-III epimer ratio (Table 3.)

Amount of ((S)-Taddol 1 molar equivalent, amount of MeMgBr 3.5 molar equivalents, reaction temperature: (−)-50° C.)

TABLE 3

| Solvent | Epimer ratio (S)-III:(R)-III | Estimated yield (%) |
|---|---|---|
| Ether | 65:35 | 85 |
| Methyl tert-butyl ether | 65:35 | 30 |
| Dimethoxyethane | 65:35 | 90 |
| Methyl-THF | 61:39 | 95 |
| Tetrahydrofuran | 61:39 | 98 |
| Dichloromethane | 65:35 | 90 |
| Chloroform | 38:62 | 35 |
| Toluene | 70:30 | 98 |

Surprisingly, the best epimer ratio, beside a very good yield, was achieved not in an ether-type solvent, typical for Grignard reactions, but in toluene, (S)-III: (R)-III=70:30.

Especially interesting is that in chloroform the S/R selectivity turned to reverse.

To accomplish the reactions an excess of 3.5 molar equivalents of Grignard reagent, methylmagnesium bromide was chosen. Thus, in our process less Grignard reagent is used than in the process described in patent specification WO2008/081191, where the Grignard reagent (MeMgCl) was applied in an excess of 5 molar equivalent.

A further advantage is that the reaction is performed at higher temperature, at (−)-50° C., instead of the (−)-78° C. applied in the cited patent specification.

We also investigated the effect of the concentration. In the studied region (5, 8 and 10-times excess of solvent), however, the concentration did not influence the epimer ratio. The most appropriate solvent excess was 8-times excess. More concentrated reaction mixtures were difficult to agitate, whereas in more diluted solutions the reaction slowed down.

We found in surprise, that in the presence of the achiral triethylamine the Grignard reaction performed in toluene resulted an epimer ratio of (S)-III:(R)-III=55:45, instead of the expected 50:50% ratio. Combined effect of triethylamine and (S)-Taddol, however, did not further enhance the 70:30 selectivity, achieved without the use of the base.

In the Grignard reaction the best epimer ratio (70:30) was achieved in toluene at (−)-50° C., using 3.5 molar equivalents of methylmagnesium bromide reagent and 1 molar equivalent of (S)-Taddol chiral auxiliary material.

Separation of the (S)-III and (R)-III epimers according to our present knowledge is only possible by very costly preparative HPLC, therefore at that intermediate level we did not aim separation. At the end of the reaction the reaction mixture was decomposed with diluted acid. Following work-up a significant amount of the (S)-Taddol crystallized from the mixture. The rest of (S)-Taddol was removed by filtration on silica gel column by washing with hexane-ethyl acetate and ethyl acetate eluents.

The recovered (S)-Taddol can be re-used in the stereoselective Grignard reaction.

Since separation of the epimers of III is only possible by costly preparative HPLC method, we searched for other methods for the epimer separation.

Sharpless epoxidation may generally be used for kinetic resolution of allyl alcohols. (Kinetic resolution of racemic allylic alcohols by enantioselective epoxidation. A route to substances of absolute enantiomeric purity?, V. S. Martin, S. S. Woodard, T. Katsuki, Y. Yamada, M. Ikeda, K. B. Sharpless, JACS, 103, 6237-6240 (1981).)

The basis of the separation is that in the presence of chiral auxiliary material epoxidation of the two epimeric allyl alcohols may be carried out in a manner that only the not-desired epimer forms the epoxide, while the desired epimer remains unreacted. Starting from a 1:1 epimeric mixture and using 0.5 molar equivalents of the epoxidation reagent, in an ideal case the desired epimer may be obtained in 50% yield, in a purity of 100%.

In the Sharpless epoxidation the usual oxidation agent is tert-butylhydroperoxide (TBHP), the chiral auxiliary material is the diethyl (DET) or diisopropyl ester (DIPT) of D- or L-tartaric acid, the catalyst is titanium tetraisopropylate.

In our case, in the presence of (D)-tartaric acid diisopropyl ester ((D)-DIPT) chiral auxiliary material, epoxidation of the not-desired epimer (R)-III) took place in higher rate. Starting from a 50:50% epimeric enol mixture the epimeric purity of the resulting compound of formula III was 70%.

If the epimer composition of the enol of formula III was 70:30, the epoxidation reaction did not change this ratio. This method for the separation of the epimers was therefore ruled out.

Lacton Reduction

The lacton group of the (S) 70: (R) 30 epimeric mixture of the enol III, prepared in the presence of (S)-Taddol chiral auxiliary material, was reduced under the conditions frequently used in prostaglandin chemistry, with DIBAL-H reagent, in tetrahydrofuran, at (−)-75° C.

Separation of the IV PPB-lactol epimers (mixture of 4 isomers) obtained after work-up was not successful by crystallisation in acetone, ethyl acetate, methyl tert-butyl ether, toluene-hexane mixture or in the mixtures of the above solvents.

Methanolysis

The p-phenylbenzoyl (PPB) protecting group of the lactol epimers of formula IV was removed in methanol solution, in the presence of base (potassium carbonate).

Separation of the lactol epimers of formula V (mixture of 4 isomers) obtained after work-up was not successful by crystallisation in acetone, ethyl acetate, methyl tert-butyl ether, toluene-hexane mixture or in the mixtures of the above solvents.

Wittig Reaction

Wittig reaction was carried out in tetrahydrofuran. To construct the upper chain, the lactol epimers of formula V were reacted with the phosphoran liberated from (carboxybutyl)triphenylphosphonium bromide (CBFBr) with potassium tert-butylate in tetrahydrofuran solvent. The Carboprost (R,S) of formula I gained after work-up was carried into the next, esterification step, without isolating the epimers.

Esterification

Separation of the 15-epimers seemed most promising at the Carboprost ester level, therefore we investigated in details the possibility of the epimer separation.

Our aim was to carry out the separation with the economical gravity chromatography, instead of the very costly preparative HPLC technique.

Based on TLC and HPLC studies, of the prepared esters the methyl ester was the most appropriate for the separation of the epimers.

The chromatographic purification was performed using ester-, ether- and ketone-type and halogenated solvents.

In addition to the method described in J. Am. Chem. Soc., 96(18), 5865-5876, 1974 where dichloromethane:acetone=2:1 eluent mixture was used, good separation was also achieved with ethyl acetate:methyl ethyl ketone, isopropyl acetate:methyl ethyl ketone and methyl tert-butyl ether:acetone mixtures.

For the epimer separation dichloromethane:acetone=2:1 mixture has been chosen, but based on the observation that Carboprost methyl ester decomposes on the week acidic surface of the silica gel, the following innovative changes have been introduced:

Into the eluents of the chromatographic purification 0.1% triethylamine was mixed in order to prevent decomposition of the acid-sensitive tertiary alcohol on the silica gel column.

Technological impurities of the crude Carboprost methyl ester were removed by chromatography on silica gel column using methyl tert-butyl ether:0.1% triethylamine, and methyl tert-butyl ether:acetone:0.1% triethylamine eluent mixtures.

Separation of the Carboprost methyl ester epimers was accomplished using dichloromethane:0.1% triethylamine, and dichloromethane:acetone:triethylamine=2:1:0.1% mixtures by repeated chromatography on the same chromatography column.

By repeated chromatography the amount of the undesired epimer can be decreased to the specified limit ($\leq 0.5\%$).

The evaporated main fraction which contained the undesired epimer at a level complying with the specified limit, was carried into the next step.

Between the two chromatographies the silica gel column was regenerated by washing with 0.1% triethylamine:acetone, and 0.1% triethylamine:dichloromethane eluents.

Chromatography can also be accomplished with success if a slightly basic silica gel is used. Best separation was achieved on Chromatorex MB 40-70 particle size spherical silica gel (pH value: 7.5-8.0) using acetone: dichloromethane gradient mixtures as eluents. In that case the addition of 0.1% triethylamine to the eluent mixture was not necessary.

Although the price of Chromatorex MB 40-70 particle size spherical silica gel is by one order higher than that of the irregular Geduran Si 60 0.063-0.200 mm silica gel, applying the more expensive silica gel the (R,S) epimers can be separated in one chromatography in a yield of 57% and the resulting Carboprost methyl ester contains the 15-epi isomer impurity in not more than 0.5% amount.

Hydrolysis

Carboprost methyl ester was hydrolysed to Carboprost in methanol solution by treatment with sodium hydroxide solution. Acidification to obtain the Carboprost has to be performed quickly, to avoid epimerisation in the acidic medium (Eur. J. Pharm. Sci., 3, 27-38 (1995).

Salt Formation

To form the tromethamine salt, Carboprost was dissolved in isopropanol, to the solution solid tromethamine base was added and the mixture was agitated. When salt formation completed, the reaction mixture was filtered. Carboprost tromethamine salt was crystallized by addition of acetone, ethyl acetate and hexane.

The tromethamine salt may be recrystallized in good yield.

The advantage of our method as compared to the process disclosed in patent specification US2013/0190404 A is that we don't use water and therefore, we don't need to use large quantities of solvents to precipitate Carboprost from the water.

In our method, in the presence of (S)-Taddol chiral auxiliary we reached an epimer ratio of 70:30. This selectivity is the same as described in patent specification WO 2008/081191.

All-over yields of the two processes counted from the protected PG-enones (TES-PG-enone and PPB-PG-enone, respectively) to the epimeric (R,S) ester mixtures are 75 and 86%, respectively, which means that the yield achieved in our process is by 10% higher.

Pre-purification of the crude epimeric ester mixture is carried out in both processes by gravity column chromatography, but patent specification WO 2008/081191 does not disclose the conditions of the chromatography.

Separation of the isomers in the process of patent specification WO 2008/081191 is performed by costly high pressure preparative chromatography, whereas in the process according to the present invention the isomers are separated by gravity chromatography which is time- and cost-saving and scalable.

Purification by chromatography is rendered more difficult by the fact that Carboprost methyl ester decomposes on the silica gel of acidic character. Successful separation may only be achieved if the rate of the elution is higher than that of the decomposition. This criteria is fulfilled by the expensive preparative chromatography where a relative small amount of injected material passes through the silica gel column in high rate.

Applicability of the gravity chromatography in our method is made possible by the innovative realisation comprising that into the eluent used for the chromatography 0.1% of basic additive, preferably the low boiling point organic base, triethylamine is added, which by binding to the acidic sites of the silica gel hinders the decomposition of the material to be purified on the chromatography column. Chromatography may also be performed with good efficiency if we apply a silica gel of week basic (pH=7.5-8.0) character. In that case a neutral eluent is also appropriate for the separation of the Carboprost methyl ester epimers.

Further Advantages of our Process:

The chiral catalyst is expensive, but it may be regenerated and re-used in 90-95%, while the use of triethylchlorosilane, which is also expensive, significantly increases the production costs.

The Grignard reaction is performed at a higher temperature (at −50° C., instead of −78° C.), the amount of the Grignard reagent is smaller (3.5 equ, instead of 5 equ).

In the reverse phase high pressure chromatography method, described in patent specification WO 2008/081191 as the most favourable purification process, the purified product is in the aqueous phase and further extraction steps are required to gain the product, elongating the production time. In our normal phase gravity column chromatography method the fractions satisfying quality requirements are united and evaporated to obtain the purified product.

Further details of our invention are demonstrated by the examples, without limiting the invention to the examples.

The use of at least 0.01% of basic additive is effective and the use of more than 1% of basic additive is not practical.

EXAMPLES 1.a [1,1'-Bisphenyl]-4-carboxylic acid, (3aR,4R,5R, 6aS)-hexahydro-2-oxo-4-[(1E)-3-hydroxy-3-methyl-1-octen-1-yl]-2H-cyclopenta[b]furan-5-yl ester 4.66 kg of (S)-Taddol was added to 25.4 L distilled toluene under nitrogen atmosphere. The almost homogenous solution was cooled and 25 L of 1.4 M methylmagnesium bromide solution was added at (−)-50° C. After 30 minutes of agitation the solution of 4.46 kg of [1,1'-bisphenyl]-4-carboxylic acid (3aR,4R,5R,6aS)-hexahydro-2-oxo-4-[(1E)-3-oxo-1-octen-1-yl]-2H-cyclopenta[b]furan-5-yl ester in distilled toluene was added at (−)-50° C. After completion of the reaction the mixture was poured onto the mixture of 1 M hydrochloric acid and toluene and thoroughly agitated. The phases were separated, the aqueous phase was extracted with toluene. The organic phase was washed with 1 M sodium hydrogen carbonate solution and with saturated salt solution. The organic phase was evaporated.

The dry residue was dissolved in methanol at 50° C. and then cooled to 0° C. The precipitated (S)-Taddol was removed by filtration.

The filtrate was evaporated, the residue was dissolved in toluene and the remains of (S)-Taddol were removed by filter chromatography on silica gel column using hexane: ethyl acetate and ethyl acetate eluents.

The main fraction of the chromatography containing the product was evaporated.

Yield: 4.40 kg (95%).

Recovery of (S)-Taddol 4.6 kg of (S)-Taddol re-gained by crystallisation and by chromatographic separation was dissolved in acetone at 50° C. and crystallized at 0° C. after the addition of hexane. The crystals were collected by filtration, washed and dried.

Yield: 4.3 kg (93.5%), purity by HPLC: 99.96%.

1.b [1,1'-Bisphenyl]-4-carboxylic acid, (3aR,4R,5R, 6aS)-hexahydro-2-hydroxy-4-[(1E)-3-hydroxy-3-methyl-1-octen-1-yl]-2H-cyclopenta[b]furan-5-yl ester

9.7 kg of [1,1'-Bisphenyl]-4-carboxylic acid, (3aR,4R,5R, 6aS)-hexahydro-2-oxo-4-[(1E)-3-hydroxy-3-methyl-1-octen-1-yl]-2H-cyclopenta[b]furan-5-yl ester was dissolved in 62 kg of water-free tetrahydrofuran under nitrogen atmosphere. At (−)-75° C. the toluene solution of 9.8 kg of diisobutylaluminum hydride was added. At the end of the reduction the reaction mixture was transferred by suction onto 2M sodium hydrogen sulphate solution, the phases were thoroughly mixed and separated after sedimentation. The aqueous phase was extracted with toluene, the united organic phase was washed with 1 M sodium hydrogen carbonate solution and with saturated salt solution. The organic phase was evaporated.

Yield: 9.74 kg (99.96%).

1c. 2H-Cyclopenta[b]furan-2,5-diol, hexahydro-4-(3-hydroxy-3-methyl-1-octen-1-yl)

C29H36O5
Mr: 464.61

C16H28O4
Mr: 284.40

10.3 kg of [1,1'-Bisphenyl]-4-carboxylic acid, (3aR,4R,5R,6aS)-hexahydro-2-hydroxy-4-[(1E)-3-hydroxy-3-methyl-1-octen-1-yl]-2H-cyclopenta[b]furan-5-yl ester was dissolved in 46 L of methanol, 1.5 kg of potassium carbonate was added and reacted at 40° C. After completion of the reaction the mixture was cooled to 0° C. and neutralised with diluted phosphoric acid. The precipitated crystals were filtered off, washed with methanol:water mixture and the filtrate was concentrated. To the concentrate water and sodium chloride were added. The product was extracted with ethyl acetate, the united organic phase was decolorized with active charcoal, the charcoal was filtered off and the filtrate was evaporated.

Yield: 6.1 kg (97%).

1d. Carboprost Crude (5Z,9α,11α,13E)-15-methyl-9,11,15-trihydroxy-prosta-5,13-diene-1-carboxylic acid, crude (R,S)

-continued

CBFBr
C23H24BrO2P
Mr: 443.31

20 kg of carboxybutyltriphenylphosphonium bromide (CBFBr) was added into 133 L of water-free tetrahydrofuran in an inert atmosphere, cooled to 0° C., and in several portions 17 kg of potassium tert-butylate was added to the mixture. The orange-coloured suspension was cooled to (−)-5-(−)-10° C. and the solution of 5.9 kg of 2H-cyclopenta[b]furan-2,5-diol, hexahydro-4-(3-hydroxy-3-methyl-1-octen-1-yl) in water-free tetrahydrofuran was added. After completion of the reaction water was added to the reaction mixture and with 2 M sodium hydrogen sulphate solution the pH was set to 10-11. The reaction mixture was concentrated and cooled to 20° C. The precipitated crystals were filtered off, washed with 1 M sodium hydrogen carbonate solution and with water. The filtrate was extracted with dichloromethane. The pH of the aqueous phase was set to neutral with 2 M sodium hydrogen sulphate solution, then after the addition of ethyl acetate, acidified to pH=2. The precipitated crystals were filtered off, washed with ethyl acetate. The phases of the filtrate were separated. The aqueous phase was extracted with ethyl acetate. The united organic phase was washed with saturated salt solution, dried over sodium sulphate and concentrated. The concentrate was cooled to 20° C. and crystallized by addition of diisopropyl ether. The crystals were filtered off and washed with diisopropyl ether:acetone mixture. The filtrate was evaporated.

Yield: 7.1 kg, (93%).

1e1. Carboprost Methyl Ester (5Z,9α,11α,13E,15S)-15-methyl-9,11,15-trihydroxy-prosta-5,13-diene-1-carboxylic acid methyl ester 7.7 kg of crude Carboprost (R,S) was dissolved in 28 L of distilled acetone, 9 kg of potassium carbonate and 9.1 kg of methyl iodide were added to the solution and the reaction mixture was agitated at 50° C. At the end of the reaction the mixture was transferred by suction onto the mixture of methyl tert-butyl ether and 1 M sodium hydrogen sulphate solution. Following agitation and sedimentation, the phases were separated and the aqueous phase was extracted with methyl tert-butyl ether. The united organic phase was washed with 1 M sodium hydrogen carbonate solution and with saturated salt solution, dried over sodium sulphate and evaporated. Crude product: 8 kg (100%).

Based on the above, the yield of the crude Carboprost methyl ester calculated for the PG-enone is 86%.

At the beginning of the evaporation 70 ml of triethylamine was added to the solution. The concentrate was purified by chromatography on silica gel column using methyl tert-butyl ether:triethylamine (0.1%), then methyl tert-butyl ether:acetone:triethylamine=20:1:0.1% eluent mixtures. The main fraction containing the Carboprost methyl ester epimers (R,S) was evaporated. The epimers were separated on silica gel column, using dichloromethane:triethylamine (0.1%) and dichloromethane:acetone:triethylamine=2:1: 0.1% eluent mixtures, by repeated chromatography. Between the two chromatographic cycles the silica gel column was regenerated with acetone:triethylamine (0.1%) and then with dichloromethane:triethylamine (0.1%) eluent mixtures.

The main fraction was evaporated.

Yield: for Carboprost methyl ester (VII) 2.35 kg (42%) (taking into account that the crude Carboprost methyl ester contains the epimers in 70:30 ratio).

1e2. Alternative Method for the Purification

Crude Carboprost methyl ester was dissolved in dichloromethane and purified by chromatography on Chromatorex MB70-40/75 silica gel column using dichloromethane-acetone=4:1, 2:1 gradient mixtures and then acetone eluents. The fractions containing Carboprost methyl ester were investigated by HPLC, the fractions of adequate quality were evaporated.

Yield: 2.97 kg (57.5%).

1f. Carboprost (5Z,9α,11α,13E)-15-methyl-9,11,15-trihydroxy-prosta-5,13-diene-1-carboxylic acid)

550 g of Carboprost methyl ester was dissolved in 5 L of distilled methanol and 5 L of 2N sodium hydroxide solution was added. After completion of the hydrolysis, water was added to the reaction mixture and the solution was concentrated. To the concentrated reaction mixture water and methyl tert-butyl ether were added, thoroughly mixed, then the phases were separated. To the aqueous phase sodium chloride and methyl tert-butyl ether were added and the pH was set to 4 with 2M sodium hydrogen sulphate solution. The phases were separated, the aqueous phase was extracted with a methyl tert-butyl ether, the organic phase was washed with saturated salt solution, dried over sodium sulphate and evaporated.

Yield: 519 g, (98%).

1g. Carboprost Tromethamine

Salt of (5Z,9α,11α,13E)-15-methyl-9,11,15-trihydroxy-prosta-5,13-diene-1-carboxylic acid formed with 2-amino-2-(hydroxymethyl)-1,3-propanediol 509 g of Carboprost was dissolved in 2.7 L of filtered, distilled isopropanol, then 170.8 g of tromethamine was added and the reaction mixture was agitated at room temperature for approx. 1 hour. The solution was filtered and concentrated. To the concentrate isopropanol (filtered, distilled) and acetone (filtered, distilled) were added. The reaction mixture was agitated at 20° C. while crystals precipitated. To the crystal suspension filtered, distilled ethyl acetate, then filtered, distilled hexane were added and agitation was continued for another hour. The crystals were filtered off, washed with hexane:acetone:ethyl acetate mixture and dried.

Yield: 593 g, (86%).

1h. Recrystallization of Carboprost Tromethamine 500 g of Carboprost tromethamine salt was dissolved in filtered, distilled isopropanol. To the obtained solution filtered, distilled acetone was added dropwise at 20° C. After the majority of the crystals precipitated, ethyl acetate (filtered, distilled) then hexane (filtered, distilled) were added and the crystal suspension was further agitated. After approx. 1 hour of agitation the crystals were filtered off, washed with hexane:acetone:ethyl acetate mixture and dried.

Yield: 480 g, 96%.

The invention claimed is:

1. A process for the preparation of Carboprost of formula I and optionally its tromethamine salt of formula Ia by selectively alkylating an enone of general formula II in a selective alkylation step with a Grignard reagent in the presence of a chiral auxiliary, in an aprotic organic solvent, to produce an enol of general formula III, wherein R is a protecting group,
reducing the enol of the general formula III to produce a lactol of general formula IV, wherein R is as defined above, removing the R protecting group of the lactol of the general formula IV, to produce lactol epimers of formula V,

V reacting the lactol epimers of formula V in a Wittig reaction to obtain Carboprost epimers of formula VI,

VI transforming the Carboprost epimers of formula VI into methyl esters of formula VII,

VII chromatographically separating the methyl ester epimers of formula VII using gravity silica gel chromatography to obtain an epimer of formula VIII,

VIII and hydrolysing of the epimer of formula VIII to provide the Carboprost of formula I, and optionally forming the tromethamine salt of formula Ia using solid tromethamine base characterized in that an eluent containing a base is used in the gravity silica gel chromatography and/or a slightly basic silica gel stationary phase is used in the gravity silica gel chromatography.

2. The process as defined in claim 1, wherein the Grignard reagent is methylmagnesium chloride or methylmagnesium bromide.

3. The process as defined in claim 2, wherein the Grignard reagent is methylmagnesium bromide which is present at 3-4 molar equivalents.

4. The process as defined in claim 1, wherein the chiral auxiliary is a complex-forming chiral auxiliary.

5. The process as defined in claim 4, wherein the complex-forming chiral auxiliary is (S)-Taddol.

6. The process as defined in claim 5, wherein (S)-Taddol is used in 1 molar equivalent amount.

7. The process as defined in claim 1, wherein the R protecting group is selected from the group consisting of ether-, silyl ether-, benzyl-, substituted benzyl-, and acyl-groups.

8. The process as defined in claim 7, wherein the R protecting group is p-phenylbenzoyl.

9. The process as defined in claim 1, wherein the aprotic organic solvent is ethers, aromatic hydrocarbons, halogenated solvents, or a mixture thereof.

10. The process as defined in claim 9, wherein the aprotic organic solvent is toluene.

11. The process as defined in claim 1, wherein the selective alkylation step is carried out at (−)-80-(−)-20° C.

12. The process as defined in claim 1, wherein the eluent containing a base is used in the gravity silica gel chromatography and the base is triethylamine.

13. The process as defined in claim 12, wherein the amount of the triethylamine is 0.1% by volume.

14. The process as defined in claim 12, wherein the eluent is a mixture of: dichloromethane and triethylamine or a mixture of dichloromethane, acetone, and triethylamine.

15. The process as defined in claim 1, wherein a slightly basic silica gel stationary phase is used in the gravity silica gel chromatography and an acetone-dichloromethane gradient mixture is used as the eluent.

16. The process as defined in claim 1, wherein tromethamine salt formation is carried out in water-free polar organic solvent.

17. The process as defined in claim 16, wherein the polar organic solvent is selected from alcohols and/or ketones.

18. The process as defined in claim 2, wherein the Grignard reagent is methylmagnesium bromide.

19. The process as defined in claim 3, wherein the methylmagnesium bromide is present at 3.5 molar equivalents.

20. The process as defined in claim 9, wherein the aprotic organic solvent is selected from the group consisting of diethyl ether, methyl tertiary-butyl ether, diisopropyl ether, tetrahydrofuran, methyltetrahydrofuran, dimethoxyethane, benzene, toluene, xylene, dichloromethane, and a mixture thereof.

21. The process as defined in claim 11, wherein the selective alkylation step is carried out at (−)-50° C.

22. The process as defined in claim 1, wherein the eluent containing a base is used in the gravity silica gel chromatography and the base is an organic base or ammonia.

23. The process as defined in claim 17, wherein the polar organic solvent is isopropyl alcohol and/or acetone.

* * * * *